US008133667B2

(12) United States Patent
Shapero et al.

(10) Patent No.: US 8,133,667 B2
(45) Date of Patent: *Mar. 13, 2012

(54) METHODS FOR GENOTYPING WITH SELECTIVE ADAPTOR LIGATION

(75) Inventors: Michael H. Shapero, Redwood City, CA (US); Keith W. Jones, Sunnyvale, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/272,370

(22) Filed: Nov. 17, 2008

(65) Prior Publication Data

US 2009/0075345 A1    Mar. 19, 2009

Related U.S. Application Data

(63) Continuation of application No. 11/381,125, filed on May 1, 2006, now Pat. No. 7,452,671.

(60) Provisional application No. 60/676,058, filed on Apr. 29, 2005.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .......... 435/6; 435/91.2; 536/23.1; 536/24.3
(58) Field of Classification Search ............. 435/6, 91.2, 435/6.1; 536/23.1, 24.3
See application file for complete search history.

(56) References Cited

U.S. PATENT DOCUMENTS

| | | | |
|---|---|---|---|
| 5,002,867 A | 3/1991 | Macevicz | |
| 5,143,854 A | 9/1992 | Pirrung et al. | |
| 5,202,231 A | 4/1993 | Drmanac et al. | |
| 5,387,505 A | 2/1995 | Wu | |
| 5,492,806 A | 2/1996 | Drmanac et al. | |
| 5,498,535 A | 3/1996 | Fomenkov et al. | |
| 5,501,964 A | 3/1996 | Wigler et al. | |
| 5,508,169 A | 4/1996 | Deugau et al. | |
| 5,580,730 A | 12/1996 | Okamoto | |
| 5,582,989 A | 12/1996 | Caskey et al. | |
| 5,624,825 A | 4/1997 | Walker et al. | |
| 5,667,972 A | 9/1997 | Drmanac et al. | |
| 5,695,940 A | 12/1997 | Drmanac et al. | |
| 5,700,637 A | 12/1997 | Southern | |
| 5,700,642 A | 12/1997 | Monforte et al. | |
| 5,710,000 A | 1/1998 | Sapolsky et al. | |
| 5,776,753 A | 7/1998 | Hillman et al. | |
| 5,854,033 A | 12/1998 | Lizardi | |
| 5,858,656 A | 1/1999 | Deugau et al. | |
| 5,972,693 A | 10/1999 | Rothberg et al. | |
| 5,994,068 A | 11/1999 | Guilfoyle et al. | |
| 6,045,994 A | 4/2000 | Zabeau et al. | |
| 6,100,030 A | 8/2000 | McCasky Feazel et al. | |
| 6,197,510 B1 | 3/2001 | Vinayagamoorthy | |
| 6,232,066 B1 | 5/2001 | Felder et al. | |
| 6,258,539 B1 | 7/2001 | Hunkapiller et al. | |
| 6,280,935 B1 | 8/2001 | Macevicz | |
| 6,280,950 B1 | 8/2001 | Lipshutz et al. | |
| 6,322,971 B1 | 11/2001 | Chetverin et al. | |
| 6,352,828 B1 | 3/2002 | Brenner | |
| 6,355,431 B1 | 3/2002 | Chee et al. | |
| 6,361,947 B1 | 3/2002 | Dong et al. | |
| 6,509,160 B1 | 1/2003 | Sapolsky et al. | |
| 6,703,228 B1 | 3/2004 | Landers et al. | |
| 6,720,179 B1 | 4/2004 | Macevicz | |
| 6,773,886 B2 | 8/2004 | Kaufman et al. | |
| 6,777,187 B2 | 8/2004 | Makarov et al. | |
| 6,812,005 B2 | 11/2004 | Fan et al. | |
| 7,108,976 B2 | 9/2006 | Jones et al. | |
| 7,452,671 B2 * | 11/2008 | Shapero et al. ................ | 435/6 |
| 2003/0036069 A1 | 2/2003 | Su | |
| 2004/0067493 A1 | 4/2004 | Matsuzaki et al. | |
| 2004/0110153 A1 | 6/2004 | Dong et al. | |
| 2005/0100911 A1 | 5/2005 | Patil et al. | |
| 2005/0148004 A1 | 7/2005 | Wolber et al. | |
| 2006/0063158 A1 | 3/2006 | Dong et al. | |
| 2006/0073501 A1 | 4/2006 | Van Den Boom et al. | |
| 2006/0246457 A1 | 11/2006 | Dirks et al. | |
| 2007/0065816 A1 | 3/2007 | Dong et al. | |

FOREIGN PATENT DOCUMENTS

EP     0534858     3/1993

(Continued)

OTHER PUBLICATIONS

Nspl in New England BioLabs Catalog (2010).*
Nakano et al., Adaptor Polymerase Chain Reaction for single molecule amplification. J. of Bioscience and Bioengineering 100(2) : 216-218 (2005).*
Broude et al., High Level Mulitplex DNA Amplification; *Antisense & Nucleic Acid Drug Development*, 2001, 11: 327-332.
Broude et al., Mulitplex Allele-Specific Target Amplifcation Based on PCR Suppression, *PNA*, Jan. 2, 2001, 98:1, 206-211.
Craig et al., Removal of Repetitive Sequences from FISH probes using PCR-assisted affinity chomatography; Human Genetics, vol. 100, No. 3-4, 1997, pp. 472-476.

(Continued)

*Primary Examiner* — Ethan Whisenant
(74) *Attorney, Agent, or Firm* — Sandra Wells (57) ABSTRACT

The present invention provides methods for reducing the complexity of a nucleic acid sample to interrogate a collection of target sequences. Complexity reduction can be accomplished by fragmenting the nucleic acid sample with a restriction enzyme that has at least one variable position in the recognition sequence. In some aspects adaptors that ligate to some but not all possible overhangs generated by digestion are ligated to the fragments. This selective adaptor ligation allows for selective amplification of a subset of the fragments using primers complementary to the adaptor sequence. In another aspect primers that are complementary to a subset of the fragments after adaptor ligation are used for amplification. Amplified fragments may be analyzed to genotype polymorphisms by hybridization to an array of probes that are complementary to target sequences that will be amplified.

7 Claims, 3 Drawing Sheets

FOREIGN PATENT DOCUMENTS

| | | |
|---|---|---|
| EP | 1350853 | 10/2003 |
| WO | WO 96/41893 | 12/1996 |
| WO | WO 01/88174 | 11/2001 |

OTHER PUBLICATIONS

Durm et al., Fast-painting of Human Methaphase Spreads Using a Chromosome-Specific, Repeat-Depleted DNA Library Probe; Biotechniques, Eaton Publishing; Vo. 24; No. 5; May 1988; pp. 820-825.

Siebert et al., An Improved PCR Method for Walking an Uncloned Genomic DNA, *Nucleic Acids Research*, 1995, 23:6, 1087-1088.

Patel et al., A novel and rapid method for isolating sequences adjacent to rare cutting sites and their use in physical mapping. Nucleic Acids Research 19(16): 4371-4375 (1991).

Smith DR. Ligation Mediated PCR of restriction fragments from large DNA molecules. PCR methods and Applications 2: 21-27 (1992).

Szybalski et al; Class-IIS restriction enzymes—a review Gene 100: 13-26 (1991).

\* cited by examiner

Fig. 1

METHODS FOR GENOTYPING WITH SELECTIVE ADAPTOR LIGATION

RELATED APPLICATIONS

This application claims the priority of U.S. Provisional Application No. 60/676,058 filed Apr. 29, 2005, the entire disclosure of which is incorporated herein by reference in its entirety.

FIELD OF THE INVENTION

The disclosed methods are related to the area of genome analysis. In particular the methods are related to reducing the complexity of a genomic sample in a predictable and reproducible manner.

BACKGROUND OF THE INVENTION

Single nucleotide polymorphisms (SNPs) have emerged as the marker of choice for genome wide association studies and genetic linkage studies. Building SNP maps of the genome will provide the framework for new studies to identify the underlying genetic basis of complex diseases such as cancer, mental illness and diabetes. Identification of the genetic polymorphisms that contribute to susceptibility for common diseases will facilitate the development of diagnostics and therapeutics, see Carlson et al., *Nature* 429:446-452 (2004). Whole-genome association studies will be important to identification of polymorphisms with disease associations. These studies require the analysis of much denser panels of markers than are required for linkage analysis in families and will require technologies that facilitate the analysis of hundreds of thousands of polymorphisms, see, The International HapMap Consortium, *Nature* 426, 789-796 (2003).

SUMMARY OF THE INVENTION

Methods for reducing the complexity of a genomic DNA sample using selective adaptor ligation and selective amplification are disclosed. In a preferred aspect, a restriction enzyme that has a variable sequence in the recognition site is used to cleave the genomic DNA. The variable position is positioned so that when the enzyme cleaves the variable position is within the single stranded overhang that is generated. Selective adaptors that are complementary to one or some of the overhangs but not complementary to all of the overhangs may be ligated to the fragments. The adaptor ligated fragments can be amplified using primers complementary to the selective adaptor.

Different adaptors may be used to ligate to different overhangs and the different adaptors may contain different primer binding sites. For example, if the variable position can be any of the 4 bases, A, G, C or T then there are 4 possible overhangs that can be generated. Each of the four can be targeted by a different selective adaptor. The selective adaptors will vary at the position in the overhang in the adaptor that is complementary to the variable position in the fragment. The selective adaptors may also vary at the priming site they contain so that each adaptor can be amplified using a different primer. In another aspect, two or more adaptors share the same primer binding site. Different subsets of the genomic DNA may be amplified depending on the selective adaptors used and the primers used for amplification.

In some aspects the variable position can be an A or G, a C or T, an A or T, or a C or G. Exemplary restriction enzymes include, Sty1, Nsp1, BsaJ1 and Dde1.

In another aspect a method for genotyping known sequence variants in a genomic DNA sample is disclosed. The complexity of the sample is first reduced by fragmenting the genomic DNA sample with a restriction enzyme that has a degenerate recognition sequence and generates variable overhangs, ligating selective adaptors to at least some of the overhangs and amplifying some of the fragments. The amplified fragments are further fragmented, labeled with a detectable label and hybridized to an array of allele specific probes that are perfectly complementary to one allele of a known sequence variant. The hybridization pattern obtained from the array is analyzed to determine the genotype of at least some of the known sequence variants.

In another aspect kits for reducing the complexity of a genomic DNA sample are disclosed. The kits include at least one restriction enzyme that has a degenerate recognition sequence and at least one selective adaptor and at least one primer complementary to the selective adaptor. The kits also contain an array of allele specific probes complementary to known sequence variants. In a preferred aspect the kit contains selective adaptors for each of the overhangs generated by the restriction enzyme and the adaptors each have a different priming sequence.

DETAILED DESCRIPTION OF THE INVENTION a) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series (Vols. I-IV)*, *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "Oligonucleotide Synthesis: A Practical Approach" 1984, IRL Press, London, Nelson and Cox (2000), *Lehninger, Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252, 743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Patent Application Publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871, 928, 5,902,723, 6,045,996, 5,541,061, and 6,197,506. Additional methods of genotyping, complexity reduction and nucleic acid amplification are disclosed in U.S. patent application Ser. Nos. 60/508,418, 60/468,925, 60/493,085, 09/920,491, 10/442,021, 10/654,281, 10/316,811, 10/646, 674, 10/272,155, 10/681,773, 10/712,616, 10/880,143, 10/891,260 and 10/918,501 and U.S. Pat. No. 6,582,938.

The present invention also contemplates sample preparation methods in certain preferred embodiments. Prior to or concurrent with genotyping, the genomic sample may be amplified by a variety of mechanisms, some of which may employ PCR. See, for example, *PCR Technology: Principles and Applications for DNA Amplification* (Ed. H. A. Erlich, Freeman Press, New York, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. Ser. No. 09/513, 300, which are incorporated herein by reference.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861, 245), nucleic acid based sequence amplification (NABSA), rolling circle amplification (RCA), multiple displacement amplification (MDA) (U.S. Pat. Nos. 6,124,120 and 6,323, 009) and circle-to-circle amplification (C2CA) (Dahl et al. Proc. Natl. Acad. Sci 101:4548-4553 (2004). Other amplification methods that may be used are described in, U.S. Pat. Nos. 5,242,794, 5,494,810, 5,409,818, 4,988,617, 6,063,603 and 5,554,517 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Ser. Nos. 09/916,135, 09/920,491 (U.S. Patent Application Publication 20030096235), 09/910,292 (U.S. Patent Application Publication 20030082543), and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y., 1989); Berger and Kimmel *Methods in Enzymology*, Vol. 152, *Guide to Molecular Cloning Techniques* (Academic Press, Inc., San Diego, Calif., 1987); Young and Davism, *P.N.A.S*, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096;

6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. Nos. 10/389,194, 60/493,495 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See U.S. Pat. No. 6,420,108.

The present invention may also make use of various computer program products and software for a variety of purposes, such as probe design, management of data, analysis, base calling, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Methods for analyzing array data to make genotyping calls are described, for example, in Di et al. Bioinformatics, 2005 Jan. 18. See also U.S. Pat. No. 6,586,186

Additionally, the present invention may have preferred embodiments that include methods for providing genetic information over networks such as the Internet as shown in U.S. Ser. Nos. 10/197,621, 10/063,559 (United States Publication Number 20020183936), 10/065,856, 10/065,868, 10/328,818, 10/328,872, 10/423,403, and 60/482,389.

b) Definitions

The term "adaptor" refers to an oligonucleotides of at least 10, 15, 20 or 25 bases and preferably no more than 100 bases in length and more preferably no more than 50 to 60 bases in length, that may be attached to the end of a nucleic acid. Adaptor sequences may be synthesized using any methods known to those of skill in the art. They may comprise, for example, priming sites, the complement of a priming site, recognition sites for endonucleases, common sequences and promoters. The adaptor may be entirely or substantially double stranded. A double stranded adaptor may comprise two oligonucleotides that are at least partially complementary. The adaptor may be phosphorylated or unphosphorylated on one or both strands. In preferred aspects the adaptor has a double stranded section and a single stranded overhang section that is completely or partially complementary to an overhang generated by a restriction enzyme. The overhang in the adaptor may be, for example, 4 to 8 bases. For example, when DNA is digested with the restriction enzyme EcoRI the resulting double stranded fragments are flanked at either end by the single stranded overhang 5'-AATT-3', an adaptor that carries a single stranded overhang 5'-AATT-3' will hybridize to the fragment through complementarity between the overhanging regions. This "sticky end" hybridization of the adaptor to the fragment facilitates ligation of the adaptor to the fragment, however, blunt ended ligation is also possible. Blunt ends can be converted to sticky ends using the exonuclease activity of the Klenow fragment. For example when DNA is digested with PvuII the blunt ends can be converted to a two base pair overhang by incubating the fragments with Klenow in the presence of dTTP and dCTP. Overhangs may also be converted to blunt ends by filling in an overhang or removing an overhang.

In many aspects adaptors may be ligated to restriction fragments. Methods of ligation will be known to those of skill in the art and are described, for example, in Sambrook et at. (2001) and the New England BioLabs catalog. Methods include using T4 DNA Ligase which catalyzes the formation of a phosphodiester bond between juxtaposed 5' phosphate and 3' hydroxyl termini in duplex DNA or RNA with blunt and sticky ends; Taq DNA Ligase which catalyzes the formation of a phosphodiester bond between juxtaposed 5' phosphate and 3' hydroxyl termini of two adjacent oligonucleotides which are hybridized to a complementary target DNA; *E. coli* DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3' to 5' phosphodiester bond, substrates include single-stranded RNA and DNA as well as dinucleoside pyrophosphates; or any other methods described in the art. Different enzymes generate different overhangs and the overhang of the adaptor can be targeted to ligate to fragments generated by selected restriction enzymes.

In some embodiments a double stranded adaptor is used and only one strand is ligated to the fragments. Ligation of one strand of an adaptor may be selectively blocked. Any known method to block ligation of one strand may be employed. For example, one strand of the adaptor can be designed to introduce a gap of one or more nucleotides between the 5' end of that strand of the adaptor and the 3' end of the target nucleic acid. Absence of a phosphate from the 5' end of an adaptor will block ligation of that 5' end to an available 3'OH. For additional adaptor methods for selectively blocking ligation see U.S. Pat. No. 6,197,557 and U.S. Ser. No. 09/910,292 which are incorporated by reference herein in their entirety for all purposes.

Adaptors may also incorporate modified nucleotides that modify the properties of the adaptor sequence. For example, phosphorothioate groups may be incorporated in one of the adaptor strands. A phosphorothioate group is a modified phosphate group with one of the oxygen atoms replaced by a sulfur atom. In a phosphorothioated oligo (often called an "S-Oligo"), some or all of the internucleotide phosphate groups are replaced by phosphorothioate groups. The modified backbone of an S-Oligo is resistant to the action of most exonucleases and endonucleases. Phosphorothioates may be incorporated between all residues of an adaptor strand, or at specified locations within a sequence. A useful option is to sulfurize only the last few residues at each end of the oligo. This results in an oligo that is resistant to exonucleases, but has a natural DNA center.

The term "admixture" refers to the phenomenon of gene flow between populations resulting from migration. Admixture can create linkage disequilibrium (LD).

The term "allele" as used herein is any one of a number of alternative forms a given locus (position) on a chromosome. An allele may be used to indicate one form of a polymorphism or variant, for example, a biallelic SNP may have possible alleles A and B. An allele may also be used to indicate a particular combination of alleles of two or more SNPs in a given gene or chromosomal segment. The frequency of an allele in a population is the number of times that specific allele appears divided by the total number of alleles of that locus.

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to beads, silica chips, or other solid supports.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference. Perfectly complementary is used to refer to complementarity of two nucleic acids without mismatch or gap.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "genotype" as used herein refers to the genetic information an individual carries at one or more positions in the genome. A genotype may refer to the information present at a single polymorphism, for example, a single SNP. For example, if a SNP is biallelic and can be either an A or a C then if an individual is homozygous for A at that position the genotype of the SNP is homozygous A or AA. Genotype may also refer to the information present at a plurality of polymorphic positions.

The term haplotype refers to groups of adjacent SNPs that tend to be inherited together as a group. These regions of linked variants represent detectable organization on chromosomes and can be used to maximize genotyping information. For example, identification of the genotype of a "tagSNP" from within a haplotype can be used to infer the genotype of nearby SNPs.

The term "Hardy-Weinberg equilibrium" (HWE) as used herein refers to the principle that an allele that when homozygous leads to a disorder that prevents the individual from reproducing does not disappear from the population but remains present in a population in the undetectable heterozygous state at a constant allele frequency.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than about 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations or conditions of 100 mM MES, 1 M [Na$^+$], 20 mM EDTA, 0.01% Tween-20 and a temperature of 30-50° C., preferably at about 45-50° C. Hybridizations may be performed in the presence of agents such as herring sperm DNA at about 0.1 mg/ml, acetylated BSA at about 0.5 mg/ml. As other factors may affect the stringency of hybridization, including base composition and length of the complementary strands, presence of organic solvents and extent of base mismatching, the combination of parameters is more important than the absolute measure of any one alone. Hybridization conditions suitable for microarrays are described in the Gene Expression Technical Manual, 2004 and the GeneChip Mapping Assay Manual, 2004.

The term "hybridization probes" as used herein are oligonucleotides capable of binding in a base-specific manner to a complementary strand of nucleic acid. Such probes include peptide nucleic acids, as described in Nielsen et al., Science 254, 1497-1500 (1991), LNAs, as described in Koshkin et al. Tetrahedron 54:3607-3630, 1998, and U.S. Pat. No. 6,268, 490 and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (for example, total cellular) DNA or RNA.

The term "isolated nucleic acid" as used herein mean an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

The term "ligand" as used herein refers to a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (for example, opiates, steroids, etc.), hormone receptors, peptides, enzymes, enzyme substrates, substrate analogs, transition state analogs, cofactors, drugs, proteins, and antibodies.

The term "linkage analysis" as used herein refers to a method of genetic analysis in which data are collected from affected families, and regions of the genome are identified that co-segregated with the disease in many independent families or over many generations of an extended pedigree. A disease locus may be identified because it lies in a region of the genome that is shared by all affected members of a pedigree.

The term "linkage disequilibrium" as used herein refers to the preferential association of a particular allele or genetic marker with a specific allele, or genetic marker at a nearby chromosomal location more frequently than expected by chance for any particular allele frequency in the population. For example, if locus X has alleles A and B, which occur equally frequently, and linked locus Y has alleles C and D, which occur equally frequently, one would expect the combination AC to occur with a frequency of 0.25. If AC occurs more frequently, then alleles A and C are in linkage disequilibrium. Linkage disequilibrium may result from natural selection of certain combination of alleles or because an allele has been introduced into a population too recently to have reached equilibrium with linked alleles. The genetic interval around a disease locus may be narrowed by detecting disequilibrium between nearby markers and the disease locus. For additional information on linkage disequilibrium see Ardlie et al., Nat. Rev. Gen. 3:299-309, 2002. See also, Thomas, Cancer Epidemiol. Biomarkers Prev. 15: 595-598 (2006) for a discussion of genome-wide association studies.

The term "lod score" or "LOD" is the log of the odds ratio of the probability of the data occurring under the specific hypothesis relative to the null hypothesis. LOD=log [probability assuming linkage/probability assuming no linkage].

The term "mixed population" or sometimes refer by "complex population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

The term "monomer" as used herein refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "receptor" as used herein refers to a molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

A number of methods disclosed herein require the use of one or more "restriction enzymes or endonucleases" to fragment the nucleic acid sample. In general, a restriction enzyme recognizes a specific nucleotide sequence of four to eight nucleotides and cuts the DNA at a site within or a specific distance from the recognition sequence. For example, the restriction enzyme EcoRI recognizes the sequence GAATTC and will cut a DNA molecule between the G and the first A. The length of the recognition sequence is roughly proportional to the frequency of occurrence of the site in the genome. A simplistic theoretical estimate is that a six base pair recognition sequence will occur once in every 4096 ($4^6$) base pairs while a four base pair recognition sequence will occur once every 256 ($4^4$) base pairs. If an enzyme with a variable position in the recognition site is used this changes the frequency of occurrence. For example, Sty1 has recognition site CCWWGG where W can be A or T so a theoretical estimate for the frequency of occurrence of the site is once every 1024 ($4^4 \times 2^2$) bases. In silico digestions of sequences from the Human Genome Project show that the actual occurrences may be more or less frequent, depending on the sequence of the restriction site. Because the restriction sites are rare, the appearance of shorter restriction fragments, for example those less than 1000 base pairs, is much less frequent than the appearance of longer fragments. Many different restriction enzymes are known and appropriate restriction enzymes can be selected for a desired result. For a comprehensive list of many commercially available restriction enzymes, their recognition sites and reaction conditions see, New England BioLabs Catalog which is herein incorporated by reference in its entirety for all purposes.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

c) Complexity Reduction Using Selective Adaptor Ligation (SAL)

Variation at the DNA in the human genome has been demonstrated to be a valuable tool that can be used to discover genetic variants involved in disease and to characterize and predict individual responses to therapeutic agents. One of the most abundant forms of DNA variation in humans is single nucleotide variants. These variants can be common, occurring with a minor allele frequency (MAF) of at least 5% across the entire human population, somewhat rare, occurring at an MAF of 1 to 5% in the population, or they can be very rare, with a MAF of less than 1%. Those single nucleotide variants that occur with a MAF of at least 1% are often called single nucleotide polymorphisms or SNPs. There are more than 5 million SNPs in the human genome and because of linkage adjacent SNPs are often inherited together in what is known as a haplotype. SNPS within the haplotype that can be used to uniquely identify the haplotype can be defined as tagSNPs. Methods for genotyping large numbers of single nucleotide polymorphisms provide powerful tools necessary for whole genome studies to map the location of polymorphisms associated with particular phenotypes. Methods that are based on hybridization of the genome to an array of hundreds of thousands or millions of different probes often benefit from a reduction of the complexity of the starting material in order to reduce non-specific binding and increase the ratio of signal to noise. Reducing the complexity improves the specificity and reliability of detection but reduces the amount of information that can be interrogated. For example, if the complexity is reduced to 10% of the original complexity only the markers that are in that 10% can be interrogated. Whole genome association studies ideally interrogate hundreds of thousands of SNPs and in a preferred embodiment more than 500,000 SNPs so a minimum level of complexity is required. Also, the complexity must be sufficient to allow for some markers that not suitable for association studies due to, for example, poor performance in the assay, proximity to another SNP, or very low minor allele frequency (MAF). Methods that reduce the overall sequence complexity but retain information of interest, for example, retaining large numbers of polymorphisms are disclosed.

One method that has been used for complexity reduction is to fragment the sample with one or more restriction enzymes, ligate an adaptor to the fragments and then amplify the fragments that fall within a size range, for example, about 200 to 2500 base pairs. This Whole Genome Sampling Assay (WGSA) has been successfully used, in combination with a high density array of allele specific probes, to genotype more than 10,000 SNPs (see, for example, Mastsuzaki et al, *Gen. Res.* 14:414-425, 2004) and more than 100,000 SNPs (see, for example, Klein et al., *Science* 308(5720):385-9, (2005). Fragments that are longer are not efficiently amplified because of their length and fragments that are smaller than about 200 are not efficiently amplified because of self complementarity between the ends of each strand. In this way part of the sample can be amplified while reducing the overall complexity. Information in the amplified portion of the sample can be interrogated, for example by hybridization to an array of allele specific probes. This method of reducing complexity has been termed a Whole Genome Sampling Assay (WGSA) and allows for amplification of a representative subset of a selected genome. The fragments that will be amplified can be predicted by analyzing the sequence and the position of the restriction sites for the enzyme or enzymes used for fragmentation using in silico digestion methods. This method is used for genotyping pre-selected sets of human SNPs by the Affymetrix 10K Mapping arrays and the Affymetrix 100K Mapping set. These arrays allow genotyping of more than 10,000 and more than 100,000 human SNPs respectively. The GeneChip 100K Mapping array set currently enables researchers to genotype more than 500,000 human SNPs by allele specific hybridization. For each SNP to be genotyped a probe set is designed for each of the A and B alleles. The A probe set includes probes that are perfectly complementary to the A allele and the B probe set includes probes that are perfectly complementary to the B allele. Mismatch control probes may also be included and the probes may be shifted so that the base that is complementary to the SNP is moved from the central position or 0 position to the left or right by 1 to 7 bases. These arrays and methods of using the arrays are described in detail, for example, in U.S. patent application Ser. No. 11/406,880.

In one aspect of the present invention genomic DNA is digested with at least one restriction enzyme that has at least one degenerate position in the recognition sequence. Preferably the enzyme cuts to generate an overhang that includes at least one degenerate position. The overhang may be 1 to 3 bases but is more preferably 4 or more bases. In a preferred aspect the overhang is 4 bases and one or two are variable. Adaptors may be ligated to some or all of the resulting fragments and adaptor-ligated fragments are amplified using a primer or primers complementary to the adaptor sequence. The methods provide ways for managing the complexity of genomic samples. For example, in one aspect the methods may be used to provide a sample with a complexity that is between the complexity obtained when genomic DNA is digested with a restriction enzyme that has a 6 base pair recognition sequence and the complexity resulting from digestion with an enzyme with a 4 base pair recognition sequence. The complexity generated, for example, when the human genome is cut with XbaI (recognition site TCTAGA) is about 288 Mb and within that fraction there are about 280,000 known SNPs. When the enzyme is Sty I (recognition site CCWWGG where W is A or T) the complexity is approximately 542 Mb and there are about 1,080,000 SNPs in that fraction. Because of the degenerate base in the overhang left after digestion, the complexity of the resulting amplified fraction can be further modulated by using adaptors or primers that target a subset of the sequences generated. In this way different subsets of the 1,080,000 SNPs can be amplified and analyzed using the same restriction digest but different adaptors. Also, the restriction fragments generated by a more frequent cutter, such as StyI or NspI, are smaller on average than those fragments generated by a 6 cutter and the smaller fragments amplify more efficiently by PCR.

Reducing the complexity of the sample prior to hybridization may be used to improve signal to noise but reduces the number of sequences that can be interrogated. The methods disclosed herein provide for reduction in complexity by amplification of sequences of interest. The flexibility provided by the use of degenerate enzyme recognitions sites allows for amplification of sets of informative markers in the same or in different amplification reactions. The disclosed complexity reduction methods may be combined with current methods for genotyping that are able to genotype large numbers of SNPs simultaneously, by providing samples that have sufficient complexity to allow genotyping of hundreds of thousands of SNPs.

The recognition site for the enzyme Dde I is GTNAG, where N can be A, C, G or T. The possible combinations of sequences recognized by Dde I are CTAAG, CTCAG, CTGAG and CTTAG. Digestion with Dde I generates 3 base pair 5' overhangs with the sequence 5' TNA 3'. The possible resulting overhangs are TAA, TCA, TGA and TTA. Restriction fragments resulting from Dde I digestion can have 16 possible combinations of Dde I sites (any one of the 4 possible sites on either of the two ends).

In one aspect genomic DNA is fragmented with a restriction enzyme that contains at least one degenerate position in the restriction site and an adaptor that has at least one degenerate position, corresponding to a degenerate position in the restriction site is ligated to the fragments. A subset of the fragments is amplified using a primer that is complementary to the adaptor. In some aspects the adaptor may be degenerate and ligate to all or a collection of the overhangs and the primer can be selective. The primer may include the degenerate position and may be complementary to only some of the fragments.

Figure 1:
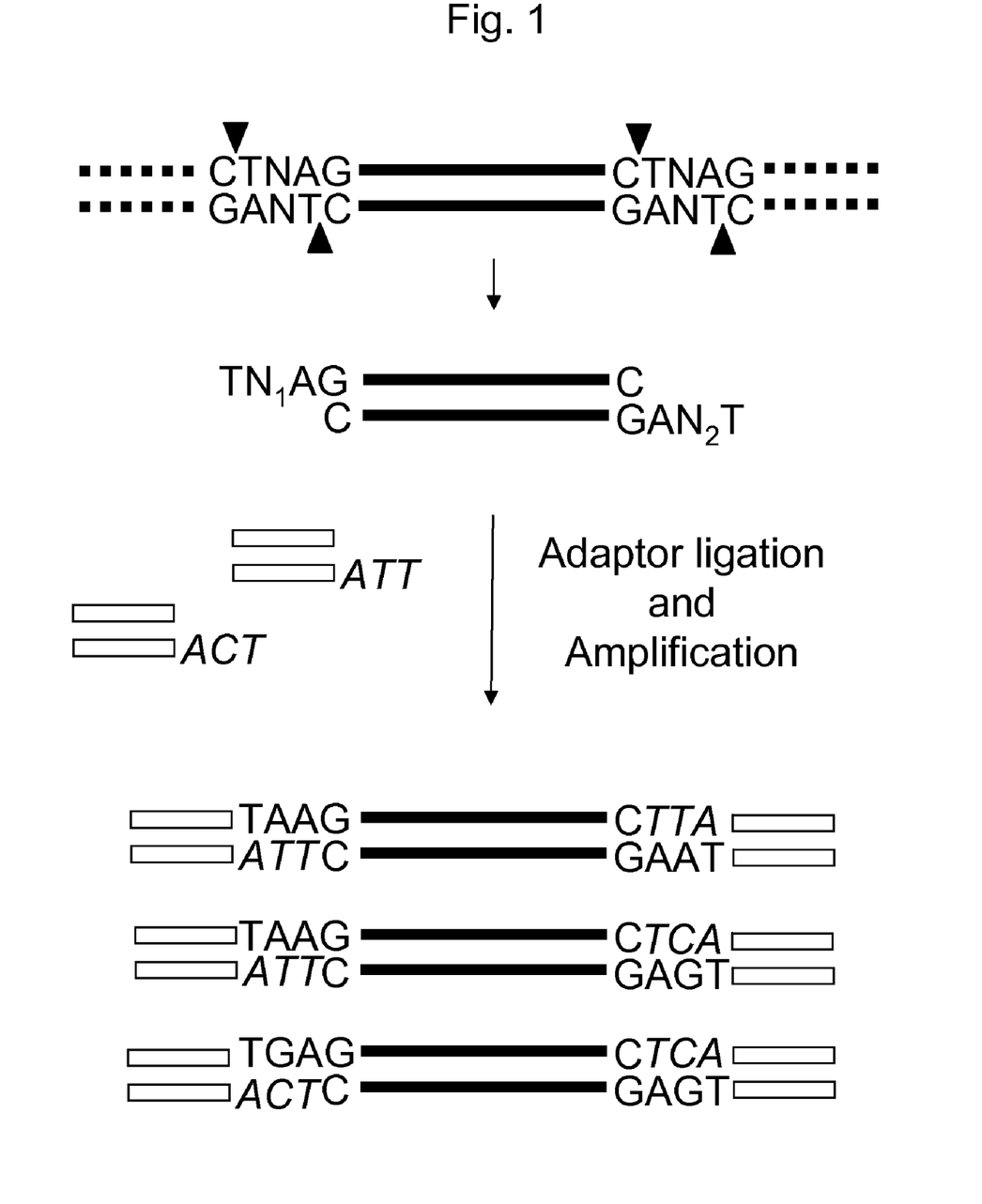
FIG. 1 shows a schematic of selective adapter ligation (SAL). The restriction enzyme used to digest the DNA recognizes a restriction site that includes a degenerate base. The adaptors used for ligation include a subset of the possible complementary overhangs and ligate to a subset of the fragments so a subset of the fragments are amplified.

Selective adaptor ligation may be used to control the complexity by varying the adaptors that are included in the ligation. FIG. 1 shows an example where the enzyme DdeI is used to digest the genomic DNA. DdeI has a recognition site GTNAG where N can be A, G, C or T. Restriction fragments resulting from DdeI will be flanked on both ends by a DdeI overhang. The two overhangs may have any of the ten possible combinations of two of the four possible bases at the $N_1$ and $N_2$ positions. The ten possible combinations for $(N_1, N_2)$ are (A,A), (A, G), (A,C), (A,T), (G,G), (G, C), (G, T), (C, C), (C, T) and (T, T). In FIG. 1 adaptors with a T or C at the position complementary to the N are included during the ligation so they ligate to restriction sites that had either an A or a G at the N (A, A), (A, G) and (G, G). For the fragment to be amplified it should have the adaptor sequence ligated to both ends so if a single adaptor sequence is added, for example, with an overhang of ATT only 10% of the fragments are targets for amplification (only those fragments that have the 5'-TAA-3' overhang on both ends. If two adaptor overhangs are used, for example 3'-ATT-5' and 3'-ACT-5' approximately 30% of the fragments will be targets for amplification (those fragments that have either 5'-TAA-3' on both ends, those fragments that have 5'-TGA-3' on both ends or fragments that have 5'-TAA-3' on one end and 5'-TGA-3' on the other end. Different combinations of adaptors may be used to amplify different collections of fragments and to interrogate the polymorphisms in those different collections. The population of polymorphisms that are present on fragments that have A or G at the N position on both ends is different from the population of polymorphisms that are present on fragments that have C or T at the N position on both ends.

Figure 2:
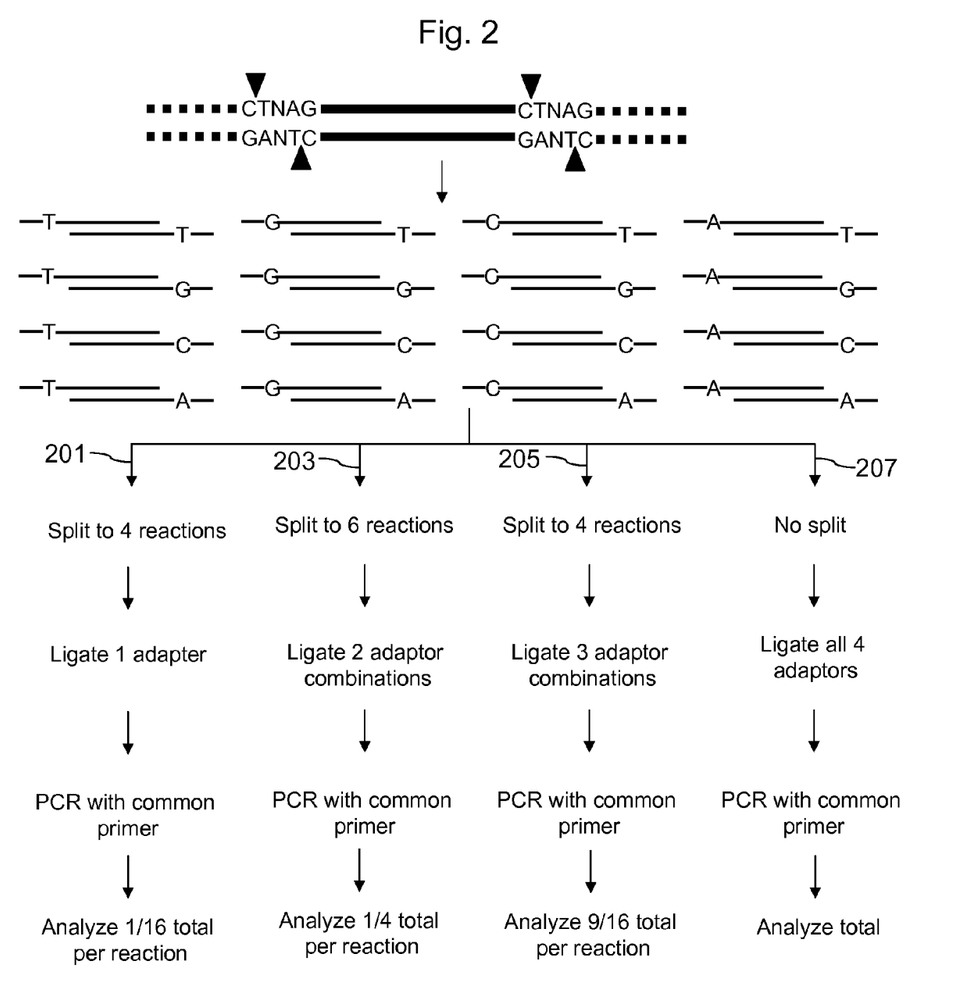
FIG. 2 shows the 16 possible overhang combinations generated when DNA is cleaved with DdeI and mechanisms of analyzing different fractions of the genome.

The different possible combinations of ends generated by cleavage with DdeI are further illustrated in FIG. 2. There are 16 possible combinations, but TG and GT are equivalent as are CT and TC, AG and GA, AC and CA, TA and AT and GC and CG, so there are 10 distinguishable combinations possible. Different combinations of adaptors can be used to modulate the complexity and change the fragments in the amplified sample using the same restriction digestion. For an enzyme with 4 different overhangs possible there are 4 different combinations of 1 adaptor, 6 combinations of 2 adaptors, 4 combinations of 3 adaptors and 1 combination of all 4 adaptors. The complexity resulting also varies although in general the single adaptor gives lowest complexity, then 2 adaptors, then 3 adaptors, and 4 adaptors giving the highest complexity. There is also variation in the relative occurrence of each sequence so some single adaptors give higher complexity than others.

Figure 3:
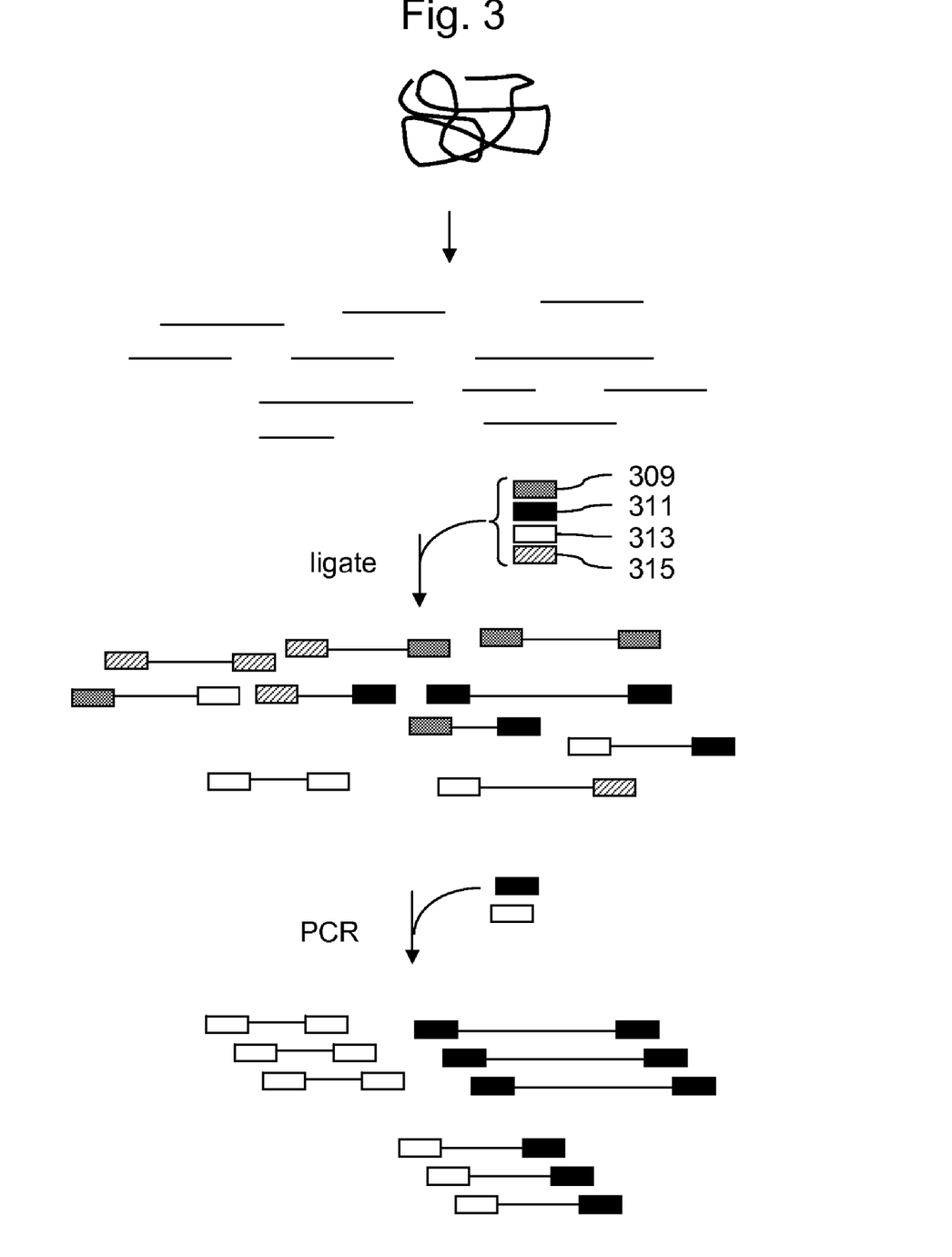
FIG. 3 shows cleavage, ligation of different overhang specific selective adaptors and amplification of a subset of fragments.

FIG. 3 illustrates that different overhangs can be ligated to different selective adaptors (309, 311, 313 and 315) and then different populations of fragments can be amplified using primers complementary to the different adaptors. In the example shown, primers to adaptors 311 and 313 are used for amplification so only those fragments that have adaptors 311 and 313 at both ends can be amplified.

The sequence of the human genome and many other organisms is known and publicly available so computer simulations of restriction digests can be used to predict the fragments that will be amplified and to identify the polymorphisms that will be in the amplified fraction, given a selected combination of adaptor sequences.

The use of selective ligation of adaptors allows for many different possible combinations that can be used to alter and control the complexity of the resulting amplification product. For example, an adaptor that is complementary to only one of the possible sequences left by digestion may be used. If there is a single degenerate position that can be any of the 4 possible bases and the adaptor is complementary to just one of the 4 possible overhangs then about 25% of the restriction sites will have the adaptor ligated to them and only those fragments that have the adaptor ligated to both ends will amplify. This is approximately $\frac{1}{16}^{th}$ of the fragments as illustrated in FIG. 2 (201). If adaptors complementary to two of four overhangs are used ¼ of the fragments can be amplified in a single reaction (203). If 3 of the overhangs are amplified $\frac{9}{16}$ of the total can be analyzed (205). The selection may be done at the ligation step so that only the desired overhangs are targeted for amplification or it can be done at the amplification step as shown in FIG. 3 so that all overhangs are ligated to adaptors but only a subset of the adaptors are amplified. The methods add an additional layer of complexity reduction to the size based complexity reduction of the WGSA. Different combinations of adaptors and different combinations of restriction enzymes can be used to amplify different subsets of the genome for analysis.

In another embodiment an enzyme with more than one degenerate base in the recognition sequence may be used, for example, BsaJ1 may be used. The recognition site for BsaJ1 is C'CNNGG. The 5' overhang after digestion is CNNG where both N's can be either A, C, G or T. There are 16 different overhangs possible. Adaptors can be selected to target different populations of fragments for amplification and analysis. Using in silico digestion methods the fragments that will be amplified when a particular adaptor or combination of adaptors is used can be predicted based on the sequence. Those fragments that will be amplified are possible targets and SNPs that are within those fragments are targets for genotyping.

In some embodiments selective adaptor ligation is combined with AFLP (Keygene, NV). AFLP is described in U.S. Pat. Nos. 6,045,994 and 6,300,071. In the AFLP method one of the primers used to amplify adaptor ligated fragments is complementary in part to at least one base within the restriction fragment and outside of the recognition site for the restriction enzyme. Because this base is outside of the recognition site it can be any of the four possible bases.

In some aspects the genomic DNA sample may be amplified prior to complexity reduction. Amplification methods, include, for example, MDA, which is disclosed in U.S. Patent Pub. No. 20030143599 and 20030040620, or any other non-specific amplification method. Kits are available for this type of amplification, for example, the REPLI-g kit from Qiagen.

In a preferred embodiment the target is genotyped by allele specific hybridization of the target DNA to a high density SNP genotyping microarray. The amplified genomic DNA is also suitable for other methods of locus specific genotyping analysis. Other methods include, for example, single base extension and allele specific extension. The amplified sample may be analyzed by any method known in the art, for example, MALDI-TOF mass spec, capillary electrophoresis, oligo ligation assay (OLA), dynamic allele specific hybridization (DASH) or TAQMAN (Applied Biosystems, Foster City, Calif.). For addition methods of genotyping analyses and references describing other methods see Syvanen, *Nature Rev. Gen.* 2:930-942 (2001) which is herein incorporated by reference in its entirety. The amplified DNA may also be used in genotyping methods such as those disclosed in Barker et al. *Gen. Res* 14:901-907 (2004).

In another aspect SAL may be used for analysis of epigenetic modifications, for example, methods for using SAL for methylation analysis are described in U.S. patent application Ser. No. 60/7444,705 filed Apr. 12, 2006.

The disclosed methods may be used to generate a reduced complexity sample for a variety of analysis methods. The methods can be used to obtain an amplified sample from a limited amount of starting genomic sample that can be analyzed by hybridization to a plurality of different probes. Different fractions of a genome can be amplified from the same digest and ligation reaction by using overhang specific adaptors and primers that are specific for the different adaptors. The portion of the genome that will be amplified when a particular enzyme and adaptor ligation scheme is used can be predicted by in silico digestion using the publicly available sequence of the genome of interest. For example, a computer may be used to model the digestion of the human genome with DdeI to predict the sequence of the fragments. The computer may also be used to predict the overhangs on either end of each predicted fragment. The computer may then be used to identify those fragments that have the overhang sequence TAA at both ends of the fragment. If only adaptors with overhang ATT are added at the ligation step only those fragments with TAA overhangs at both ends will be amplified. The computer may be used to identify those fragments and to predict the fragments that will be amplified. Those fragments may be analyzed to identify features of interest for interrogation. Those features may include SNPs but they may also be other features of interest, for example, cites of potential methylation, or positions of deletion or insertion. Downstream analysis assays may be designed to interrogate the features of interest predicted to be amplified given the restriction enzyme used and the adaptor or adaptors ligated to the fragments.

EXAMPLE

Selective Adaptor Ligation Using Dde1 and 2 or 3 of the 4 Possible Adaptors

Different combinations of adaptors were ligated to Dde1 digested genomic DNA and hybridized to either the 50K Xba or 50K HindIII Mapping arrays from Affymetrix, according to the manufacturers instructions. Only a subset of the SNPs that are interrogated by each array are predicted to be on Dde1 fragments in the size range that will be amplified and for each combination of adaptors. For each combination of adaptors a set of SNPs that could be genotyped was identified but only a subset of those met the criteria for selection after analysis of the genotyping results. The conversion rate represents the percentage of SNPs that could be genotyped that actually were genotyped with a minimum call rate and concordance. For each condition, 30 genomic DNA samples were genotyped.

To determine the conversion rate for a sample using 3 of 4 possible adaptors the samples were digested with Dde1 and ligated to adaptors complementary to the Dde1 overhangs with either an A, G or T at the variable position. The adaptor ligated fragments were amplified by PCR using a primer complementary to all three adaptors. Of 17,224 overall possible SNPs on the array that are on Dde1 fragments between 200 and 800 base pairs 582 or 3.4% met the criteria for selection. Selected SNPs are SNPs that pass three selection criteria: genotype call in at least 85% of the 30 DNA samples, a minor allele frequency that is at least 1 out of the 60 independent chromosomes tested (30 individuals times two chromosomes per individual) and a Hardy-Weinberg value greater than 0.00001. The overall possible number of SNPs is the number of SNPs predicted to be on Dde1 200-800 bp fragments amplified using the selected adaptors. HapMap release 14 was used to assess the accuracy of the DM algorithm based genotyping calls.

To determine conversion rate when 2 of 4 adaptors were used, the Dde1 digested samples were ligated to adaptors complementary to the Dde1 overhangs with a T or C in the variable position in a first reaction or a G or A in the variable position in a second reaction. For the T and C adaptors there were 10,876 possible SNPs and 1083 or 10.0% met the criteria for selection. For the G and A adaptors there were a possible 10,178 SNPs and of those 1140 or 11.2% met the criteria for selection.

The results indicate that genotyping results, measured in conversion percentages, were improved when the lower complexity sample (2 of 4 possible adaptors) was used relative to a higher complexity sample (3 of 4 possible adaptors).

CONCLUSION

It is to be understood that the above description is intended to be illustrative and not restrictive. Many variations of the invention will be apparent to those of skill in the art upon reviewing the above description. The scope of the invention should be determined with reference to the appended claims, along with the full scope of equivalents to which such claims are entitled. All cited references, including patent and non-patent literature, are incorporated herewith by reference in their entireties for all purposes.

We claim:

1. A method for analyzing a genomic DNA sample comprising:
   reducing the complexity of the sample by:
   (a) fragmenting the sample with a restriction enzyme that has a recognition sequence that comprises at least one fixed position and has a variable region consisting of one or two variable positions, wherein the at least one fixed position and the variable region are in the single-stranded overhang generated by cleavage with the restriction enzyme and cleavage generates a plurality of single-stranded overhangs of different sequence including at least a first overhang and a second overhang;
   (b) ligating a first selective adaptor comprising a single-stranded overhang that is perfectly complementary to the first overhang and a second selective adaptor comprising a single-stranded overhang that is perfectly complementary to the second overhang to a subset of the fragments to generate adaptor-ligated fragments, wherein the first selective adaptor is perfectly complementary to and ligates with a first subset of the single-stranded overhangs generated in step (a) and is not perfectly complementary to and does not ligate with a second subset of the single-stranded overhangs generated in step (a), wherein the second selective adaptor is perfectly complementary to and ligates with a third subset of the single-stranded overhangs generated in step (a) and is not perfectly complementary to and does not ligate with a fourth subset of the single-stranded overhangs generated in step (a) and wherein the first and second selective adaptors comprise a common priming sequence; and
   (c) amplifying at least some of the adaptor-ligated fragments by polymerase chain reaction using a primer that is complementary to the common priming sequence in the first and second selective adaptors to obtain amplified fragments that are a subset of the fragments; and
   analyzing the amplified fragments by hybridization to an array of probes.

2. The method of claim 1 wherein the one or two variable positions are an N, where N is A, G, C or T.

3. The method of claim 1 wherein the one or two variable positions are an R, where R is A or G.

4. The method of claim 1 wherein the one or two variable positions are a Y, where Y is C or T.

5. The method of claim 1 wherein the one or two variable positions are a W, where W is A or T.

6. The method of claim 1 wherein the one or two variable positions are an S, where S is C or G.

7. The method of claim 1 wherein the restriction enzyme is selected from the group consisting of Sty1, BsaJ1 and Dde1.

* * * * *